(12) United States Patent
Melker et al.

(10) Patent No.: US 7,755,494 B2
(45) Date of Patent: Jul. 13, 2010

(54) HAND WASHING COMPLIANCE DETECTION SYSTEM

(75) Inventors: Richard J. Melker, Gainesville, FL (US); Nikolaus Gravenstein, Gainesville, FL (US); Donn M. Dennis, Gainesville, FL (US); Christopher D. Batich, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 326 days.

(21) Appl. No.: 11/760,100

(22) Filed: Jun. 8, 2007

(65) Prior Publication Data

US 2008/0303658 A1  Dec. 11, 2008

(51) Int. Cl.
*G08B 23/00* (2006.01)
(52) U.S. Cl. ............ 340/573.1; 340/573.6; 340/539.11; 340/539.12
(58) Field of Classification Search ................ 340/573.1
See application file for complete search history.

(56) References Cited

U.S. PATENT DOCUMENTS

| | | | |
|---|---|---|---|
| 4,706,493 A | 11/1987 | Chang et al. | |
| 4,952,928 A * | 8/1990 | Carroll et al. | ............ 340/10.41 |
| 5,610,589 A * | 3/1997 | Evans et al. | ............ 340/573.1 |
| 5,793,653 A | 8/1998 | Segal | |
| 5,952,924 A * | 9/1999 | Evans et al. | ............ 340/573.1 |
| 6,009,333 A | 12/1999 | Chaco | |
| 6,038,331 A * | 3/2000 | Johnson | ............ 382/100 |
| 6,154,139 A | 11/2000 | Heller | |
| 6,211,788 B1 | 4/2001 | Lynn et al. | |
| 6,236,317 B1 | 5/2001 | Cohen et al. | |
| 6,392,546 B1 | 5/2002 | Smith | |
| 6,417,773 B1 | 7/2002 | Vlahos et al. | |
| 6,426,701 B1 | 7/2002 | Levy et al. | |
| 6,524,390 B1 | 2/2003 | Jones | |
| 6,572,564 B2 | 6/2003 | Ito et al. | |
| 6,647,649 B2 | 11/2003 | Hunt et al. | |
| 6,727,818 B1 | 4/2004 | Wildman et al. | |
| 6,814,816 B2 * | 11/2004 | Achar et al. | ............ 134/26 |

(Continued)

FOREIGN PATENT DOCUMENTS

GB  2 324 397  10/1998

(Continued)

OTHER PUBLICATIONS

Boyce, John M., et al., "Guideline for Hand Hygiene in Health-Care Settings," *MMWR Recommendations and Reports*, Oct. 25, 2002, 51(RR16);1-44.

*Primary Examiner*—Travis R Hunnings
(74) *Attorney, Agent, or Firm*—Timothy H. Van Dyke; Beusse Wolter Sanks Mora & Maire

(57) ABSTRACT

Systems and methods are provided for monitoring use of hand washing agents to determine compliance with hand hygiene guidelines. A hand washing agent is provided with a detectable, volatile compound, such as odors, which is then rubbed onto a subject's hands using the subject's hand washing technique. After the hand washing event, the subject's hand is then exposed to a detector (such as a badge), which includes a sensor capable of detecting the volatile compound, and an indicator that communicates detection of the volatile compound, indicating use of the hand washing agent and hand hygiene compliance.

4 Claims, 3 Drawing Sheets

U.S. PATENT DOCUMENTS

| | | |
|---|---|---|
| 6,838,992 B2 | 1/2005 | Tenarvitz |
| 6,882,278 B2 | 4/2005 | Winings et al. |
| 6,970,574 B1 | 11/2005 | Johnson |
| 7,015,816 B2 | 3/2006 | Wildman et al. |
| 7,034,677 B2 | 4/2006 | Steinthal et al. |
| 7,095,501 B2 | 8/2006 | Lambert et al. |
| 7,171,312 B2 | 1/2007 | Steinthal et al. |
| 7,236,097 B1 | 6/2007 | Cunningham |
| 7,286,057 B2 * | 10/2007 | Bolling .................. 340/573.1 |
| 7,315,245 B2 * | 1/2008 | Lynn et al. .................. 340/540 |
| 7,375,640 B1 | 5/2008 | Plost |
| 7,408,470 B2 | 8/2008 | Wildman et al. |
| 7,443,305 B2 | 10/2008 | Verdiramo |
| 7,482,936 B2 * | 1/2009 | Bolling .................. 340/573.1 |
| 2004/0001009 A1 | 1/2004 | Winings et al. |
| 2006/0071799 A1 | 4/2006 | Verdiramo |
| 2006/0273915 A1 | 12/2006 | Snodgrass |
| 2007/0008146 A1 | 1/2007 | Taylor et al. |
| 2007/0008149 A1 * | 1/2007 | Bolling .................. 340/573.1 |
| 2007/0015552 A1 * | 1/2007 | Bolling .................. 455/575.6 |
| 2007/0020212 A1 | 1/2007 | Bernal et al. |
| 2008/0031838 A1 * | 2/2008 | Bolling .................. 424/70.1 |
| 2009/0068116 A1 * | 3/2009 | Arndt .................. 424/10.3 |

FOREIGN PATENT DOCUMENTS

| | | |
|---|---|---|
| GB | 2 417 811 | 3/2006 |
| GB | 2417811 | 8/2006 |
| GB | 2 425 388 A | 10/2006 |
| JP | 62132161 | 6/1987 |
| JP | 2001292918 | 10/2001 |

* cited by examiner

Isotopes Relevant to the Indicating Hand Washing event

| Isotope | Stable, Non-radioactive | Radioactive, Unstable |
|---|---|---|
| Hydrogen | $^1H$ (protium) – 99.985%<br>$^2H$ (deuterium) = $^2H$ – 0.015% | $^3H$ (tritium) |
| Carbon | $^{12}C$ – 98.89%<br>$^{13}C$ – 1.11% | $^{14}C$ |
| Oxygen | $^{16}O$ – 99.759%<br>$^{17}O$ – 0.037% [MRI scans]<br>$^{18}O$ – 0.204% [PET scans] | $^{15}O$<br>$^{19}O$ |
| Nitrogen | $^{14}N$ – 99.63%<br>$^{15}N$ – 0.37% [biochemical tracers] | No convenient |
| Sulfur | $^{32}S$ – 95.00%<br>$^{33}S$ – 0.76%<br>$^{34}S$ – 4.22%<br>$^{36}S$ – 0.014% | $^{35}S$ (other S-based radioisotopes very short lived) |

FIG. 3

HAND WASHING COMPLIANCE DETECTION SYSTEM

BACKGROUND OF THE INVENTION

Tens of thousands of people die each year from infections acquired in hospitals. These "hospital acquired" infections, also referred to as nosocomial infections, are unrelated to a patient's initial hospital admission diagnosis. In the United States, it has been estimated that as many as one hospital patient in ten acquires a nosocomial infection, or 2 million patients a year. Estimates of annual costs related to nosocomial infection range from $4.5 billion to $11 billion and up. Studies have shown that at least one third of nosocomial infections are preventable.

Nosocomial infections due to resistant organisms are an extremely serious problem that threatens the U.S. healthcare system and the welfare of its citizens. Microbes can acquire resistance to antibiotics and antifungal and antiviral agents and as the numbers of resistant organisms increase, the number of new antimicrobial agents to treat them has not kept pace. In fact, community acquired nosocomial infections, especially methicillin resistant staphylococcus aureus (MRSA), has increased at an alarming rate.

It is has been reported that more than 50% of all nosocomial infections can be directly related to the transmission of harmful bacteria by healthcare workers who have not properly washed their hands before and after each patient contact. Thus, the best means to prevent transfer of these organisms from patient to patient and to reduce the emergence of resistant organisms is hand washing with soap and water between patient contacts. The Centers for Disease Control and Prevention (CDC) as well as other regulatory agencies recommend hand washing before and after each patient encounter. Unfortunately, reports indicate that healthcare workers adhere to hand washing guidelines less than 70% of the time. See O'Boyle, C. A. et al., "Understanding adherence to hand hygiene recommendations: the theory of planned behavior," *Am J Infect Control.*, 29(6):352-360 (2001). Numerous strategies have been attempted to increase healthcare worker compliance to hand washing, but all have been largely unsuccessful.

There are many possible reasons for non-compliance with recommended hand washing practices. For example, there may not be sufficient time to properly wash hands or wash stations may be placed in inconvenient locations. Some people simply forget to wash their hands. Others may not realize how infrequently or inadequately they comply with recommended hand washing practices. Others still may not fully understand the benefits of hand washing. Some or all of these issues may be addressed if means were provided to monitor compliance with recommended hand washing practices.

The problem of insufficient hand washing is becoming worse. Hospitals, through staff reductions, are requiring healthcare workers to attend to more patients during the healthcare provider's work shift. Additionally, high transmission rates of antibiotic resistant bacteria and viruses require greater adherence to the CDC hand washing guidelines. Hospital administrations are searching for products and services that encourage hand washing, and a means to ensure and measure compliance.

Similar concerns exist in other industries, such as those relating to the processing and preparation of food. The U.S. Food and Drug Administration's Food Code (the "Food Code") provides guidelines for preparing food and preventing food-borne illness. Retail outlets such as restaurants and grocery stores and other institutions such as nursing homes are subject to the Food Code. In addition to requiring employees to wash their hands, the Food Code requires their employer to monitor the employees' hand washing. Despite such extensive efforts to ensure that proper hand washing is performed, more than a quarter of all food-borne illnesses (estimated that food-borne diseases cause approximately 76 million illnesses, 325,000 hospitalizations, and 5,000 deaths in the United States each year) are thought to be due to improper hand washing.

Numerous inventions such as touch-free, automatic soap dispensers, faucets and hand dryers attempt to address the problem of workplace hygiene by making it easier for employees to wash and sanitize their hands. For example, U.S. Pat. No. 5,945,910 teaches systems and methods in which the dispensation of cleaning agents at a washstation are monitored, where the dispensation of cleaning agents is considered an indication of a hand washing event. Another approach is taught in U.S. Pat. No. 4,896,144 which, although not designed for measuring or checking hand washing compliance, is directed to alerting someone of the need to wash their hands. U.S. Pat. No. 5,812,059 is directed to a method and system for improving hand cleanliness, primarily in a food service environment. It discloses a reporting means worn by a worker, which is activated when the worker leaves a food handling area. The reporting means, worn by the worker, is deactivated by a deactivating device associated with a hand cleaning station, and only when it is determined that the worker has used the hand cleaning station before re-entry to the food handling area.

Even with the monitoring systems described above, unless employees are actively supervised in the washroom, however, there is usually no way to determine whether they have washed their hands. Furthermore, if the employees do wash their hands, there is no way to easily determine whether they have followed a prescribed government- and/or industry-approved regimen to ensure they washed and sanitized properly.

BRIEF SUMMARY OF THE INVENTION

The subject invention solves the needs in the art by providing systems and methods for monitoring and promoting hand hygiene practices. According to the subject invention, a system for promoting adherence to hand washing (or hygiene) guidelines comprises: a hand washing agent that includes a detectable, volatile compound (also referred to herein as a taggant); and a detector (such as a badge) that includes a sensor for detecting the volatile compound and an indicator operatively connected to the sensor that provides a signal indicating detection of the volatile compound.

An object of the subject invention is to detect volatile taggants on a subject's hands, wherein the presence of the volatile taggant is an indication of subject compliance in proper hand hygiene. In one preferred embodiment, the volatile taggant is a compound that is inconspicuous, so that when a subject applies the hand washing agent to one's hands, the volatile taggant is essentially undetectable to the subject's olfactory senses during and after the hand washing event. More preferably, the compound is detectable on the skin through the use of a sensor of the invention, even if the hand washing agent is removed via rinsing, rubbing, and/or drying. In certain embodiments, the volatile taggant is an FDA approved perfume and/or fragrance.

In operation, a subject (i.e., a healthcare provider or an employee of a restaurant) is provided with a detector (i.e., a badge) that is worn during working hours. The detector is designed to remind or alert the subject (or other interested parties, such as a monitoring agent, a customer, or a patient) that the subject has adequately washed his/her hands. The detector contains the necessary sensor to detect a volatile compound as well as an indicator to receive and communicate information from the sensor. After a hand washing event, volatile compounds from the hand washing agent are detected on the subject's hands using the sensor. If the volatile compound is detected, the indicator will communicate detection of the compound, which is a sign of subject performance in hand washing.

A resulting advantage of the subject invention is the ability to monitor hand hygiene compliance in a more cost effective and frequent manner than current systems and methods, which can involve expensive and bulky equipment.

Additional advantages of this invention will become readily apparent from the ensuing description.

BRIEF DESCRIPTION OF THE FIGURES

FIG. 3 is a table showing various isotopes that can be used as taggants in the subject invention.

DETAILED DESCRIPTION OF THE INVENTION

Figure 1:
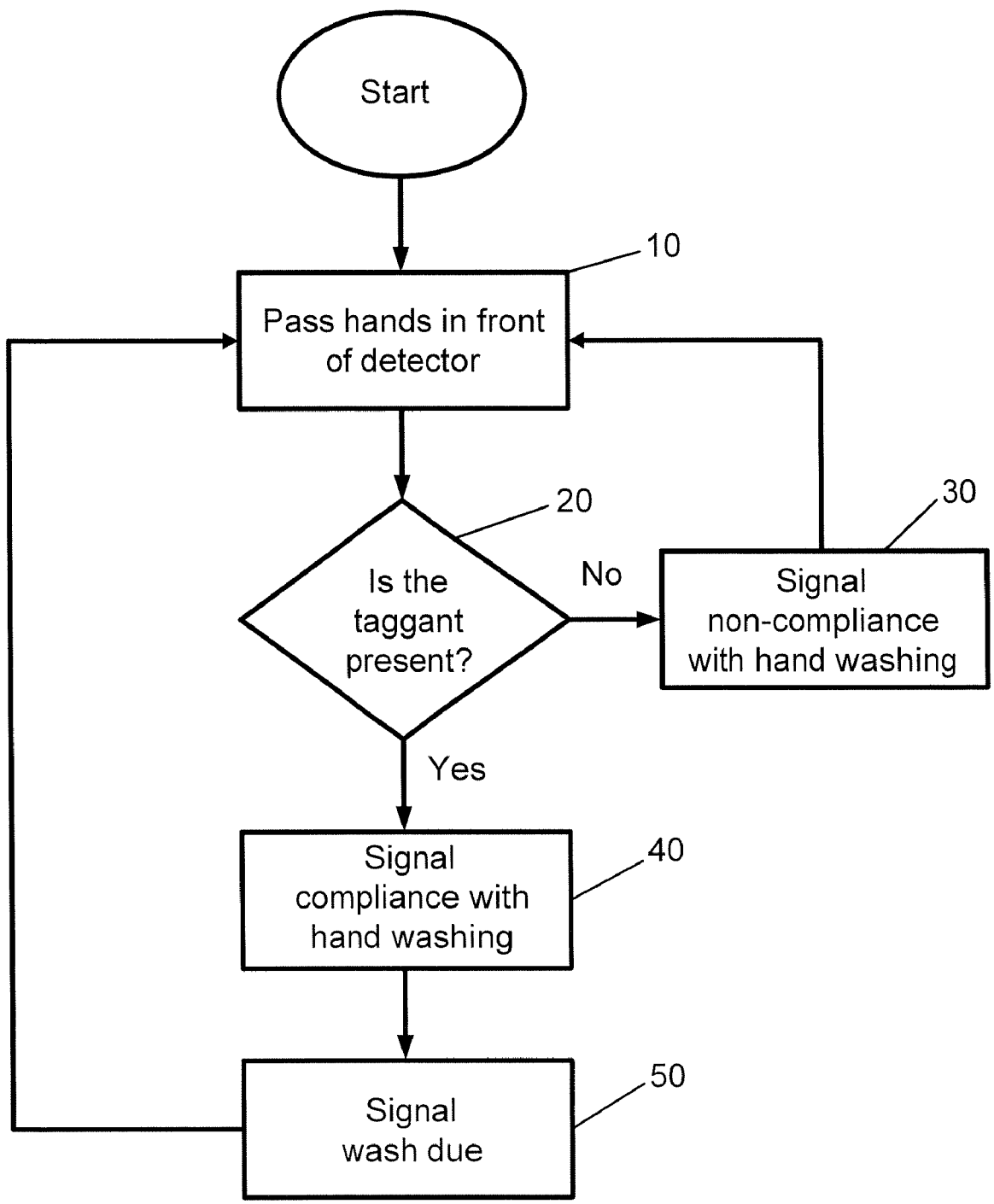
FIG. 1 is a flow chart showing operations that occur when using a detector of the invention.

The present invention provides systems and methods for monitoring proper hand hygiene activities performed by a subject by detecting a taggant on the subject's skin, where the taggant is present in a hand washing agent. The systems and methods of the invention can be practiced in any institution where hand hygiene is important. Examples of such institutions include, but are not limited to, hospitals and other health care facilities, nursing homes, restaurants and other food service institutions, food processing and manufacturing institutions, libraries, schools, airports, and the like.

A hand hygiene monitoring system of the invention comprises a hand washing agent that includes a taggant; and a detector that includes a sensor and an indicator. The system of the invention monitors hand hygiene compliance by detecting when a subject washes or rubs his/her hands with a hand washing agent that includes the taggant. Preferably, the taggant is detectable using the sensor after appropriate hand hygiene measures are taken by the subject. An indicator that is operatively connected to the sensor communicates to the subject (and/or any other interested party such as a patient or customer) whether a hand washing event has occurred within a prescribed interval. In certain embodiments, the hand hygiene monitoring system further includes a means for storing information regarding the hand washing event (i.e., storage of information regarding identity of the subject, time of hand washing event, compliance/non-compliance in hand washing event, etc.).

A method for monitoring hand hygiene compliance involves detecting the presence or absence of a taggant on a subject's skin using a detector containing a sensor; and communicating whether the taggant is present on the subject's skin using an indicator. The method can include storing and analyzing the occurrence of taggant detection (data) using a computing means. Data regarding taggant detection may be used to determine subject history (log) in hand hygiene compliance or percentage of hand hygiene compliance. In addition, the method may involve communicating whether the subject has washed his/her hands within a period of time subsequent to detection of the presence of a taggant. If a subject does not comply with appropriate hand hygiene measures, which includes using a hand washing agent that has a taggant, the method may also involve triggering a reminder alarm using the indicator.

Definitions

As used herein, the term "hand washing" or "hand hygiene" (which can be used interchangeably), refers to washing hands with a hand washing agent and water or applying a hand washing agent to all surfaces of the hand. Hand washing can include dipping hands into a hand washing agent or friction-generating activities, such as those accompanying the use of surgical scrubs that "stir up the dermis" and get down to at least 3-5 cell layers.

As used herein, the term "hand washing agent" refers to a substance used in maintaining hand hygiene (i.e., reducing the number of microorganisms on the skin). A hand washing agent of the subject invention includes, but is not limited to, alcohol-based hand rubs; antimicrobial and/or antiseptic soaps; antiseptic hand washes; antiseptic hand rubs; detergents; soaps; waterless antiseptic agents; and surgical hand scrubs. A hand washing agent may be in the form of a solid (i.e., bar of soap, surgical prep sponge), powder, liquid, cream, spray, gel, or the like.

According to the subject invention, an alcohol-based hand rub is an alcohol-containing preparation designed for application to the hands for reducing the number of viable microorganisms on the hands. Such preparations can contain about 60%-95% ethanol, isopropanol, n-propanol, or any combination of these compounds.

As used herein, an antimicrobial soap refers to a product comprising soap or detergent and an antiseptic agent.

As used herein, an antiseptic agent refers to antimicrobial substances that are applied to the skin to reduce the number of microbial flora. Examples of antiseptic agents include alcohols, chlorhexidine, chlorine, hexachlorophene, iodine, chloroxylenol (PCMX), quaternary ammonium compounds, and triclosan.

As used herein, a detergent or soap is a product that includes compounds that possess a cleaning action. They are composed of both hydrophilic and lipophilic parts and can be divided into four groups: anionic, cationic, amphoteric, and nonionic detergents. Although products used for handwashing or antiseptic handwash in health-care settings represent various types of detergents, the term "soap" also refers to such detergents.

As used herein, a waterless antiseptic agent refers to an antiseptic agent that does not require use of exogenous water. After applying such an agent, the hands are rubbed together until the agent has dried.

As used herein, an antiseptic hand wash or hand rub refers to an antiseptic-containing preparation designed for frequent use; it reduces the number of microorganisms on intact skin to an initial baseline level after adequate washing, rinsing, and drying; it is broad-spectrum, fast-acting, and if possible, persistent.

As used herein, a surgical hand scrub is an antiseptic-containing preparation that substantially reduces the number of microorganisms on intact skin; it is broad-spectrum, fast-acting, and persistent.

Throughout this disclosure, a "taggant" is defined as a substance that is detected by means of its physical or chemical properties using a sensor of the subject invention. Taggants preferably remain on the skin for a sufficient time after rinsing or drying for detection by a sensor of the invention. Taggants are preferably unique in a hand washing agent (for example, they are not molecules commonly present in hand washing agents); non-toxic to the subject; do not alter the anti-microbial, anti-viral, anti-bacterial, and/or anti-septic properties of the hand washing agent; relatively inexpensive; readily available; and easy to synthesize as well as integrate with the hand washing agent.

Hand Hygiene Monitoring System

The subject invention relates to systems for monitoring hand hygiene compliance that include a hand washing agent with a taggant and a detector, which includes a sensor and an indicator. The sensor has the ability to detect taggants on a subject's skin and the indicator communicates detection of the taggant. Communication regarding taggant detection can be immediate, as by a visual means and/or audible sound from the indicator. Further, communication regarding taggant detection can be transmitted or stored in a database, or used to alert other healthcare providers/food handlers that a subject has washed his/her hands.

According to the subject invention, taggant detection is a surrogate indication of use of the hand washing agent, and thus an indication of a hand washing event. An integral part of a system of the invention involves the communication of whether and/or when a hand washing event has occurred, as derived from monitored detection of taggants on the subject's skin, to improve subject compliance in hand hygiene.

Certain embodiments include storing and/or analyzing data regarding taggant detection (and hand washing event), including intervening with the subject when appropriate to improve compliance. Appropriateness for intervention is dependent upon the number of hand washing events detected over a period of time when compared against an expected number of hand washing events for the same period of time.

In certain embodiments, the detector includes a suction pump for directing air toward the sensors. For example, the suction pump can be used to ensure taggants from the skin are director toward the sensor(s) of the detector.

Taggants

The subject invention provides a system that monitors hand washing events. Specifically, hand washing events are monitored based on the detection of taggants on a subject's skin, where the taggant is a surrogate indicator of use of a hand washing agent. According to the subject invention, hand washing agents include a volatile, detectable taggant. Preferred taggants of the invention are those compounds with sufficient vapor pressure and volatility to be readily detectable shortly after hand washing but that would be undetectable a short time later (i.e., those taggants characterized with short persistence times). More preferably, the taggants are safe for frequent use on the skin without the potential for allergic reactions or drying of the skin.

In one embodiment, the taggants are added directly to the hand washing agent. In another embodiment, the taggants are microencapsulated or are coated or incorporated into particle/polymers, which are subsequently added to hand washing agents. Such taggants are preferably chosen from compounds that are suitable for microencapsulation, coating, or incorporating into dissolvable particles/polymers, and would remain stable until released during hand washing. Such embodiments would guarantee vigorous hand washing by the subject.

There are also many ways to incorporate taggants into water-dispersible polymers. Microencapsulated particles used to house taggants can be made using standard microencapsulation techniques including, but not limited, coacervation (i.e., complex coacervation), double emulsion (w/o/w), polymerization (i.e., interfacial, in-situ, or matrix polymerization), co-extrusion capsule formulation (i.e., drip mode, centrifugal, or jet mode co-extrusion), and air-suspension coating. For instance, in the double emulsion technique, poly L-lactic acid (PLLA) is dissolved in methylene chloride, and emulsified with an aqueous (or other incompatible solvent) containing the detectable taggant. This is adjusted to make a water in oil emulsion. This emulsion is poured into a second aqueous (or incompatible solvent) and air is bubbled through, which evaporates the organic solvent (methylene chloride), causing the PLLA to encapsulate in a hard shell, the detectable taggant. The skilled artisan would readily understand which polymers, solvents, temperature, stirring rates and surfactants should be added to optimize properties for detection in a hand washing agent. Capsules can be made to degrade or fracture under different conditions.

Preferably, volatile taggants of the invention readily evaporate and would be undetectable by human senses after a specified period of time (such as within 1 minute or within 1-5 minutes, or within 5-10 minutes) following hand washing. In accordance with the present invention, taggants that are combined with a hand washing agent include the following olfactory taggants, without limitation: dimethyl sulfoxide (DMSO), acetaldehyde, acetophenone, trans-Anethole (1-methoxy-4-propenyl benzene) (anise), benzaldehyde (benzoic aldehyde), benzyl alcohol, benzyl cinnamate, cadinene, camphene, camphor, cinnamaldehyde (3-phenylpropenal), garlic, citronellal, cresol, cyclohexane, eucalyptol, and eugenol, eugenyl methyl ether; butyl isobutyrate (n-butyl 2, methyl propanoate) (pineapple); citral (2-trans-3,7-dimethyl-2,6-actadiene-1-al); menthol (1-methyl-4-isopropylcyclohexane-3-ol); and α-Pinene (2,6,6-trimethylbicyclo-(3,1,1)-2-heptene). These taggants are preferred since they are permitted by the Food and Drug Administration. Olfactory taggants for use in the present invention can be selected from a vast number of available compounds (see *Fenaroli's Handbook of Flavor Ingredients*, $4^{th}$ edition, CRC Press, 2001) and use of such other applicable taggants is contemplated herein.

The taggants of the invention also include compounds that have been federally approved and categorized as GRAS ("generally recognized as safe"), which are available on a database maintained by the U.S. Food and Drug Administration Center for Food Safety and Applied Nutrition. Taggants categorized as GRAS that are readily detectable using a sensor of the invention include, but are not limited to, sodium bisulfate, dioctyl sodium sulfosuccinate, polyglycerol polyricinoleic acid, calcium casein peptone-calcium phosphate, botanicals (i.e., chrysanthemum; licorice; jellywort, honeysuckle; lophatherum, mulberry leaf; frangipani; selfheal; sophora flower bud), ferrous bisglycinate chelate, seaweed-derived calcium, DHASCO (docosahexaenoic acid-rich single-cell oil) and ARASCO (arachidonic acid-rich single-cell oil), fructooligosaccharide, trehalose, gamma cyclodextrin, phytosterol esters, gum arabic, potassium bisulfate, stearyl alcohol, erythritol, D-tagatose, and mycoprotein.

Additional taggants of the invention include halogenated compounds (for example, tetrachloroethane, trichloroethane, dichloroethane, dichloroethylene, trifluoroethane (Freon 113), dichloroethane, dichloropropane, 1,3-cis-dichloro-1-propene, 1,3-trans-dichloropropene, 1-chloro-2-propene, butylene dichloride, acetylene tetrachloride, bromodichloromethane, bromoform, bromomethane, carbon tetrachloride, chlorodibromomethane, chloroethane, chloroform, chloromethane, chloropropane, cis-1,2-dichloroethylene, cis-1,3-dichloropropene, dibromo-chloropropane, dibromomethane, dichlorobromomethane, dichloromethane, ethylene dibromide, fluorotrichloromethane (Freon 11), glycerol trichlorohydrin, hexachlorobutadiene, hexachlorocyclopentadiene, hexachloroethane, methylene chloride, neoprene, pentachloroethane, perchloroethylene, propylene dichloride, trichlorotrifluoroethane, monochlorobenzene, tetrachloroethylene (Perchloroethylene) (PCE), trichloroethylene (TCE), vinyl chloride, vinyl trichloride, vinylidene chloride) as well as isotopes, such as those disclosed in FIG. 3.

According to the subject invention, the taggants can have any one or combination of the following characteristics: (1) no intrinsic toxicity at concentrations required for detection by a sensor of the invention; (2) is a generally recognized as safe (GRAS) compound; (3) is an FDA approved chemical entity; (4) is unique on the skin (e.g., not found in non-hand washing agents that are applied to skin), where the taggant provides an outstanding signal to noise (S:N) ratio with a sensor of the invention, and does not require a baseline reading; (5) has rapid onset of appearance on the skin after hand washing by the subject; (6) has a reproducible duration of appearance on the skin; (7) is easily detectable by commercially available sensor technologies that are rapid, portable, inexpensive, compact, and available for real-time analysis; and (8) taggant is generated from a flexible chemistry formulation platform that will allow the selection of optimal taggants with regard to incorporation with hand washing agents and/or time of detection on a subject's skin.

Detector

The detector of the invention includes a sensor for detecting the taggant on the subject's skin; and an indicator for reporting whether the taggant was detected. According to the present invention, the detector can be presented as a badge to be worn by the subject. Preferably, the detector is implemented in a housing structure such as a card-shaped structure, badge-shaped structure, or other compact structure allowing for ease of use, transport, wearability, attachment to a subject, etc. The detector includes a sensor disposed within the badge, where said sensor has the ability to detect the presence of the taggants on the subject's skin (i.e., after the subject has soaped, scrubbed, and rinsed his/her hands using a hand washing agent of the invention); and an indicator operably connected to the sensor such that detection of the taggants by the sensor is communicated by the indicator to the subject (and/or anyone interested in assessing or monitoring subject hand hygiene).

Preferably, the detector also includes an electronic clock circuit operably connected to the indicator. In one embodiment, the electronic clock continuously generates a time signal based on taggant detection as communicated by the indicator. For example, using the electronic clock, the indicator can communicate when the last hand washing event occurred. In another embodiment, the electronic clock can be activated when the subject initiates a hand washing event and can communicate via the indicator a specified time that the subject should devote to a hand washing event. For example, the electronic clock can generate a signal for about 5 seconds up to 2 minutes that communicates to the subject the time that should be devoted to hand washing using a hand washing agent).

In certain embodiments, the detector can also include a means for processing data regarding detected taggant(s)/hand washing event, including a means for storing data regarding hand washing events and for analyzing hand washing events (i.e., comparing the number of hand washing events for a given period of time against expected number of hand washing events for the specified period of time, or against previous recorded hand washing events). Those skilled in the art will appreciate that the processing means may be implemented as electronic hardware, mechanical hardware, computer software, or combinations thereof. Whether the processing means is implemented as hardware and/or software depends upon the particular application and design constraints imposed on the overall system. Skilled artisans may implement these components in varying ways for different applications, but such implementation decisions should not be interpreted as causing a departure from the scope of the subject invention.

According to the present invention, a sensor for use in detecting taggants on skin can be operatively connected to a data processing system. The processing system is preferably programmed to assimilate and analyze output signals generated by the sensor regarding taggants detected on the skin. In one embodiment, the processing system is a computer. Taggant analysis results can be displayed on a computer screen, stored, transmitted, etc. Moreover, a computer processing unit (or CPU) may be provided as a data processing/control unit. In one embodiment, the processing unit is programmed for conducting a comparison of data regarding recommended taggant levels for a specified period of time against monitored taggant data to determine subject hand hygiene compliance.

For instance, when a physician is scheduled to see twenty patients during a clinic session, forty episodes of handwashing (handwashing should occur both before and after an encounter with a patient) should be recorded in the storage device during the time scheduled for the clinic. Less detected episodes of handwashing are indicative of behaviors that favor nosocomial infection. Likewise, if a physician or other healthcare provider is scheduled to perform a number of procedures (e.g., endoscopy, cystoscopy, bronchoscopy) during a specified time interval, two handwashing episodes, one before and after each procedure, should be detected, stored, and documented.

In one embodiment, the CPU can automatically detect and store signals from the sensor to enable proper tracking and analysis of hand washing events. The CPU may further provide to the subject (or co-workers, patients, customers, etc.) the appropriate alerts regarding hand washing events to be taken either based on pre-entered information or based on analysis of trends in hand washing events.

According to the present invention, a data analyzer can compare a pattern of response (from the sensor) to previously measured and characterized responses from known taggants. The matching of those patterns can be performed using a number of known techniques, including artificial intelligence systems (such as neural networks). By comparing analog output from a sensor (based on analyzed taggants on the skin) to a "blank" or control taggant output using, for example, a neural network, a pattern can be established that is unique to that taggant. In one embodiment, the artificial intelligence system can make an assessment of subject compliance with hand hygiene measures. Where appropriate, the artificial intelligence system can also recommend an intervention (such as increased number of hand washing events) to ensure continued subject health and prevent spread of disease due to poor hand washing hygiene.

One conventional approach that can be used in a monitoring system of the invention includes a neural network for processing data obtained from the sensor(s). As with most empirical modeling technologies, neural network development requires a collection of data properly formatted for use. Specifically, as known in the art, input data and/or the outputs of intermediate network processing layers may have to be normalized prior to use. It is known to convert the data to be introduced into a neural network into a numerical expression, to transform each of the numerical expressions into a number in a predetermined range, for example, by numbers between 0 and 1. Thus, the intelligence system of the present invention preferably has means for: 1) selecting at least a portion of the detected taggant data from the sensor data output signal; 2) converting the selected portion of the detected taggant data into numerical expressions; and 3) transforming the numerical expressions into a number in a predetermined range.

In accordance with one embodiment of the invention, the intelligence system is trained by providing to a neural network input data regarding expected number of detected taggant events based on a specified period or part thereof as well as output data from the sensors. The assessment by the intelligence system, along with the corresponding input data and output data is referred to as a data record. All available data records, possibly taken for a number of different subjects (such as male versus female; adult versus pediatric health clinician), comprise a data set. According to the present invention, a data set corresponding is stored in memory and is made available for use by the processing system for statistical, training, and/or diagnostic determinations. Normally, intelligence systems are trained ahead of time using data extracted from subjects. Using what is learned from the training data, the neural network may apply it to other/new subjects.

In another embodiment of the invention, the detector is located at a particular location (i.e., at a hand washing station, near a dispenser for hand washing agent, at a door to a patient's room, at a door to a kitchen, and the like) such that the frequency of hand washing can be compared to the frequency of entry to specific locations (i.e., entering patient access areas).

In such embodiments, a means for ascertaining subject identity is provided (i.e., by providing a code specific to the subject). Examples of identity ascertaining means include, but are not limited to, a keypad to be operated by the subject, a barcode reader, a magnetic strip reader, or any other suitable identifying device, such as radio-frequency identification technology. If the identity ascertaining means is a keypad, it should be capable of receiving codes identifying the subject. The keypad can be of any commonly available alphanumeric design known in the art. If the identity ascertaining means is a barcode reader, radio-frequency identification, or magnetic strip reader, a card or badge containing a barcode, radio-frequency identification, or magnetic strip would be issued to each subject. The subject would place the barcode, radio-frequency identification, or magnetic strip in front of or into the reader to allow the identity ascertaining means to determine the identity of the subject.

At each particular location (i.e., entrance of a restroom), the identity ascertaining means will notify a central computer system when a subject enters, and will wait for the subject to wash his/her hands before leaving. After the subject performs appropriate hand washing measures (i.e., applies the proper amount of a hand washing agent of the invention that includes taggants, rubs hands together to generate the appropriate lather), the subject waves his/her hands in front of the detector's sensor which will detect whether taggants are present on the subject's skin. In certain embodiments, the indicator can report a "pass" or "fail" reading based on the presence or absence, respectively, of the taggant on the subject's skin. The "pass/fail" information can be fed to a central computer, whereby a subject's compliance with hand hygiene measures can be determined.

In certain related embodiments, the identity ascertaining is operably connected to an entry means (i.e., a lock to a door). With such embodiments, the entry means will not permit the subject to enter or exit a location unless the detector has ascertained that the subject has performed appropriate hand hygiene measures. For example, a lock to a door to a patient's room will only disengage after "pass" reading is communicated from the indicator after a subject has waved his/her hands in front of the detector.

Sensors

According to the subject invention, any one of the many commercially available off the shelf (COTS)-based analytical approaches for measurement of analytes in gaseous phase mediums can be used to detect and/or quantify taggants on a subject's skin. These devices offer minimal cycle time, can detect multiple taggants, can work in almost any environment without special sample preparation or isolation conditions, and do not require advanced sensor design or cleansing between tests.

It is contemplated that the hand hygiene monitoring system of the invention may comprise at least one sensor, or a plurality of sensors, for capturing/detecting the desired taggant data. Each sensor generates an output signal based on the presence of the taggant(s) to an indicator. Examples of certain COTS-based approaches that can be used in accordance with the systems and methods described herein include, but are not limited to, high electron mobility transistors (HEMT), nuclear magnetic resonance (NMR), polymer based membranes—chemoresistive (Cyranose); polymer-surface acoustic wave (SAW) and electrochemical chemical array (Hazmatcad and Hazmatcad Plus); spectroscopy-based analysis; visible spectroscopy; UV spectroscopy; TIF TIFXP-1A Negative Corona Leak Detector; negative ion capture sensors; heated sensors/ceramic semiconductor sensors; infrared absorption; nuclear magnetic resonance spectroscopy; photoemission spectroscopy; Raman spectroscopy; Fourier transform spectroscopy—FTIR; time-resolved spectroscopy; flame spectroscopy; plasma emission spectroscopy; force spectroscopy; dielectric spectroscopy; circular dichroism spectroscopy; refractory indices; and the like. Other contemplated sensors include sensors based on microcantilevers, molecularly imprinted polymers, amplifying fluorescent polymers, and high electron mobility transistors. In a preferred embodiment, small scale (miniature) gas chromatography technology, which employs metal oxide (MOS) or other sensors, is used in accordance with the subject invention.

The invention preferably utilizes sensor technology, such as commercial devices known as "artificial" or "electronic" tongues or noses, to monitor taggant presence and/or concentration on a subject's skin. Electronic noses have been used mostly in the food, wine, and perfume industry where their sensitivity makes it possible to distinguish between odorous compounds. For example, electronic noses have been useful in distinguishing between grapefruit oil and orange oil in the perfume industry and in identifying spoilage in perishable foods before the odor is evident to the human nose. In a related embodiment, the sensor's particular resistor geometries can be selected to optimize the desired response to a particular taggant being sensed. For example, a self-calibrating polymeric "electronic nose" system is suitable for use in accordance with the subject invention to analyze the skin of a subject for the presence of a taggant.

A number of patents that describe gas sensor technology that can be used in the subject invention include, but are not limited to, the following: U.S. Pat. Nos. 7,171,312; 5,945,069; 5,918,257; 4,938,928; 4,992,244; 5,034,192; 5,071,770; 5,145,645; 5,252,292; 5,605,612; 5,756,879; 5,783,154; and 5,830,412; all of which are incorporated herein by reference in their entirety. Other sensors suitable for the present invention include, but are not limited to, metal-insulator-metal ensemble (MIME) sensors, cross-reactive optical microsensor arrays, fluorescent polymer films, surface enhanced Raman spectroscopy (SERS), diode lasers, selected ion flow tubes, metal oxide sensors (MOS), non-dispersive infrared spectrometer, bulk acoustic wave sensors, colorimetric tubes, functionalized microcantilevers, and infrared spectroscopy.

Recent developments in the field of detection that can also be used as sensors for the subject invention include, but are not limited to, gas chromatography, semiconductive gas sensors, mass spectrometers (including proton transfer reaction mass spectrometry), and infrared (IR) or ultraviolet (UV) or visible or fluorescence spectrophotometers (i.e., non-dispersive infrared spectrometer). For example, with semiconductive gas sensors, taggants cause a change in the electrical properties of semiconductor(s) by making their electrical resistance vary, and the measurement of these variations allows one to determine the concentration of taggant(s). In another example, gas chromatography, which consists of a method of selective detection by separating the molecules of gas compositions, may be used as a means for analyzing taggants on a subject's skin.

In accordance with the subject invention, sensors for detecting/quantifying taggants utilize a relatively brief detection time of around a few seconds. Other recent gas sensor technologies contemplated for use in a hand hygiene monitoring system of the present invention include apparatuses that utilize conductive-polymer gas-sensors ("polymeric"), aptamer biosensors, amplifying fluorescent polymer (AFP) sensors, or apparatuses having surface-acoustic-wave (SAW) gas-sensors.

Conductive-polymer gas-sensors (also referred to as "chemoresistors") have a film made of a conductive polymer sensitive to molecules of target (sometimes odorous) substances. Upon contact with target taggant molecules, the electric resistance of the sensors changes, which provides an indication of the taggant's presence. An advantage of this type of sensor is that it functions at temperatures close to room temperature. Different sensitivities for detecting different taggants can be obtained by modifying or choosing an alternate conductive polymer.

Responses of polymeric gas sensors to target taggants can be fully characterized using a combination of conventional gas sensor characterization techniques. For example, the sensor can be attached to a computer. The results can be displayed on the computer screen, stored, transmitted, etc. A data analyzer can compare a pattern of response to previously measured and characterized responses from known substances. The matching of those patterns can be performed using a number of techniques, including neural networks. The particular resistor geometries are selected to optimize the desired response to the particular taggant being sensed.

Amplifying fluorescent polymer (AFP) sensors may be utilized in the present invention for detecting the presence of taggants on a subject's skin. AFP sensors are extremely sensitive and highly selective chemosensors that use amplifying fluorescent polymers. When target taggants bind to thin films of the polymers, the fluorescence of the film decreases. A single molecule binding event quenches the fluorescence of many polymer repeat units, resulting in an amplification of the quenching. The binding of taggants to the film is reversible, therefore the films can be reused.

Surface-acoustic-wave (SAW) sensors oscillate at high frequencies and generally have a substrate, which is covered by a chemoselective material. In SAW sensors, the substrate is used to propagate a surface acoustic wave between sets of interdigitated electrodes (i.e., to form a transducer). The chemoselective material is coated on the transducer. When a taggant interacts with the chemoselective material coated on the substrate, the interaction results in a change in the SAW properties, such as the amplitude of velocity of the propagated wave. The detectable change in the characteristic wave is generally proportional to the mass load of the taggant(s) (i.e., concentration of the taggant on a subject's skin, which corresponds to the amount of hand washing agent used by the subject during a hand washing event).

Certain embodiments of the invention use known SAW devices, such as those described in U.S. Pat. Nos. 4,312,228 and 4,895,017. Other types of chemical sensors known in the art that use chemoselective coating applicable to the manufacture and operation of a hand hygiene monitoring system of the present invention include bulk acoustic wave (BAW) devices, plate acoustic wave devices, interdigitated microelectrode (IME) devices, optical waveguide (OW) devices, electrochemical sensors, and electrically conducting sensors.

In one embodiment, the sensor of the invention is based on surface acoustic wave (SAW) sensors. The SAW sensors preferably include a substrate with piezoelectric characteristics covered by a polymer coating, which is able to selectively absorb target taggants. SAW sensors oscillate at high frequencies and respond to perturbations proportional to the mass load of certain molecules. This occurs in the vapor phase on the sensor surface.

Indicator

According to the subject invention, the indicator is capable of alerting the subject as well as other interested parties (such as patients, healthcare personnel, hygiene monitoring individuals, and/or in some instances health officials) of subject compliance/non-compliance with hand hygiene measures. In certain related embodiments, the detector system is also capable of tracking/analyzing compliance based on detected hand washing events, which is associated with volatile taggant detection on the subject's skin.

The results from a sensor are provided to the subject (or anyone else interested in the subject's hand hygiene) via an indicator. Contemplated indicators include a computer processor linked to the sensor technology in which visual, audible, and/or tactile results can be provided. The indicator can include a visual light display (such as various colored lights—green, yellow, and red), digital display panel, transportable read/write magnetic media such as computer disks and tapes which can be transported to and read on another machine, and printers such as thermal, laser or ink-jet printers for the production of a printed report or can be incorporated into the detector.

The indicator can provide the results to the subject via the detector itself or via external systems, such as facsimile, electronic mail, mail or courier service, or any other means of safely and securely sending data generated by the sensor. Interactive indicators are also contemplated by the present invention, such as an interactive voice response system, interactive computer-based indicator system, interactive telephone touch-tone system, or other similar system. The report provided to the subject may take many forms, including immediate communication regarding a hand washing event; a summary of analyses performed over a particular period of time; or detailed information regarding a hand washing event. Results may also be used to populate a laboratory database or a statistical database.

Operation of a Monitoring System

As illustrated in FIG. 1, a method of using the hand hygiene monitoring system of the invention includes passing the subject's hands in close proximity to the detector 10 to detect the presence of any taggants 20; and communicating compliance or non-compliance with a hand washing event 30, 40, wherein taggant detection is a surrogate indicator of a hand washing event. In certain embodiments, after a specific period, the detector notifies the subject (and any other interested party, such as a client, patient, co-worker, etc.) that another hand washing event is due 50.

In certain embodiments, the detector can "actively" detect taggants by including a means for directing/drawing air to the sensor(s) on the detector. One such embodiment includes a suction pump on the detector that can direct air (and taggants, if present) to the sensors. The suction pump can be activated by the individual before handwashing or automatically activated by a means for establishing subject identity (such as a badge, bracelet, radio-frequency identification chip, etc.). Other embodiments of the invention would function "passively" and would not require a suction pump to detect taggants on the skin.

Taggants associated with hand washing are preferably identified by a portable, wearable detector. The detector would be worn on a lab coat or elsewhere on the person and would be activated at the time hand washing is commenced. After hand washing (either before or after drying), the taggant would be detected emanating from the hands of the subject when they are passed in proximity of the sensor in the detector. The indicator, such as with a light with various colors, would be activated should a taggant be detected by the sensor. Preferably, the indicator includes a green light indicating recently detected hand washing event; a yellow light indicating last hand washing event had occurred within a first specified period of time that is acceptable; and a red light indicating last hand washing event had occurred within second specified period of time that is unacceptable.

In a method of use, after the subject has washed his/her hands with a hand washing agent of the invention, the subject waves his/her hands in front of a detector worn by the subject. The sensor in the detector senses the taggants on the subject's skin, which would be communicated by the indicator as a green light. After an acceptable period, such as 10-15 minutes after hand washing, the indicator light on the device would turn yellow. After 10-15 minutes, the light would turn red, indicating that the last hand washing event that occurred was about 10-15 minutes ago.

Figure 2:
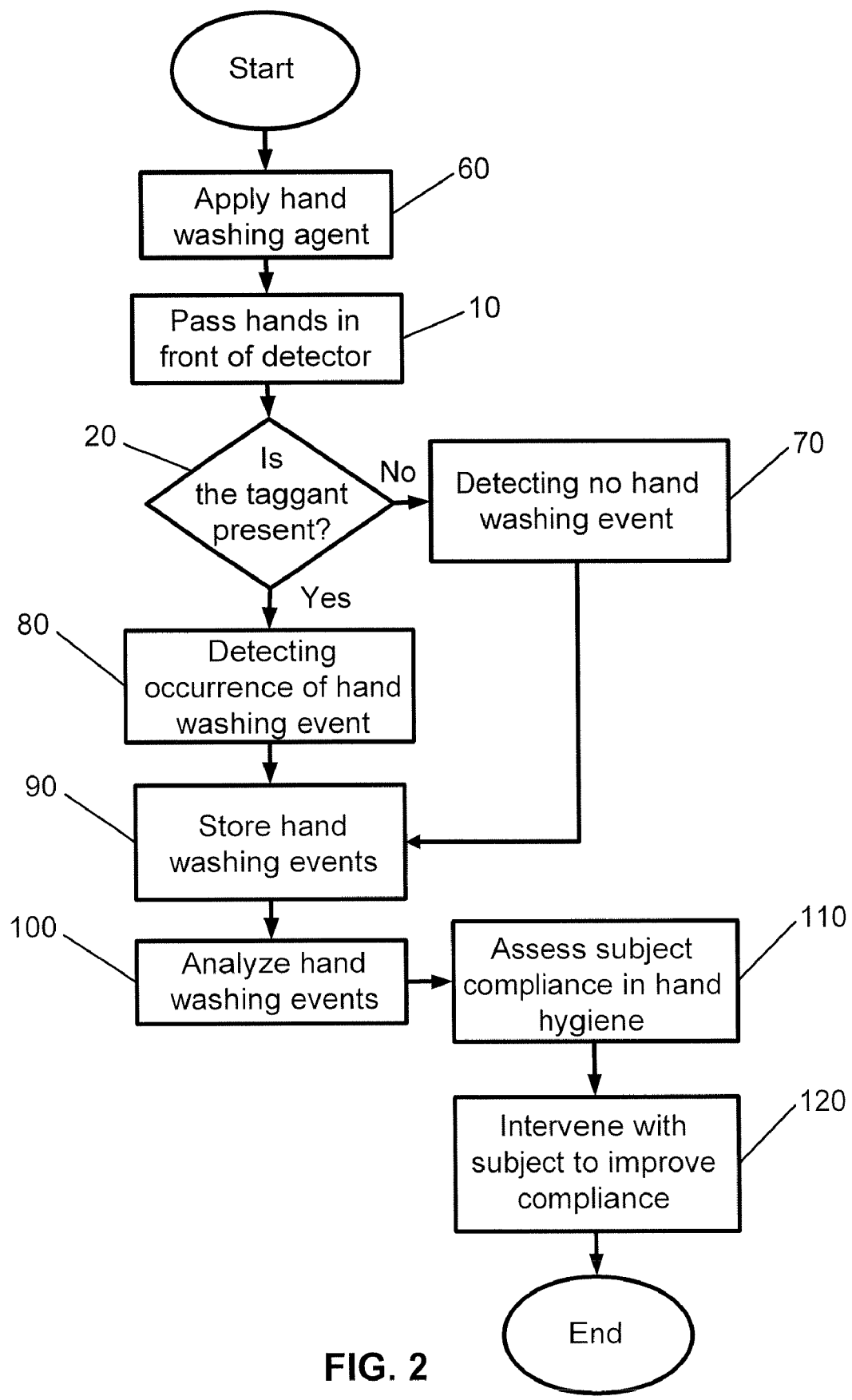
FIG. 2 is a flow chart showing operations that occur with certain embodiments of the invention.

Related methods for monitoring hand hygiene compliance can further include any one or combination of the following steps (see FIG. 2): applying hand washing agent to skin 60; detecting hand washing events 70, 80, storing 90 and/or analyzing 100 the detected hand washing events; assessing the subject's hand hygiene compliance based on the detected hand washing events 110; and intervening with the subject when appropriate to improve subject compliance 120.

In certain embodiments, in operation, the sensor will be used to identify a baseline spectrum for the subject prior to use of a hand washing agent that includes a taggant, if necessary. This will prove beneficial for the detection of the taggant where possible interference from other odors (such as perfumes in lotions) is presented.

In another embodiment, the detector and a subject identification means, which automatically detects the identification/presence of an individual by a badge, radio-frequency identification chip, etc., are mounted in close proximity to a hand washing station. When the subject approaches the subject identification means, it immediately begins a countdown process activating the detector, which must detect the presence of a taggant within a finite period after the identification means is activated or the indicator will provide feedback locally and/or remotely that the subject has not washed his/her hands.

Remote Communication System

A further embodiment of the invention includes a communications device that will be interfaced to a monitoring system of the invention. The communications device will be able to transmit immediately or at prescribed intervals via standard communication transmittal means (i.e., via satellite communication) the data collected by the system of the invention. The communication of the data will allow the interested party (i.e., hygiene monitoring personnel) to be able to verify if the subject has complied in performing hand washing using a hand washing agent of the invention and/or if the appropriate amount of a hand washing agent is being used by the subject during hand washing.

The data transmitted from the detector can also be downloaded to a computer where the detected presence of the taggant are stored in a database, and any deviations outside of the stored data is flagged so that a user could be notified of subject hand hygiene compliance. In one embodiment, the downloaded information pertains to number of times taggant was detected (or taggant levels/concentration) and deviations outside of a given number would be automatically flagged (i.e., alarm) so that a subject or other interested party (i.e., patient, physician, nurse) could address the lack of hand hygiene per suggestions provided by a computer processing unit connected to the sensor or per suggestions provided by health care personnel (i.e., hospital management personnel).

Following is an example that illustrates materials, methods, and procedures for practicing the invention. The example is illustrative and should not be construed as limiting.

Example 1

In one embodiment, a healthcare worker would dispense an adequate amount of hand soap or surgical scrub and vigorously wash the hands with water to release the encapsulated taggant. Alternatively, the microcapsules could be incorporated into "waterless" hand washing products. Prior to washing the hands, the healthcare worker would activate the detector, which would be worn in a conspicuous place so that patients could observe it, by means such as pushing a button, and then slowly wave the hands in front of the device after washing (either before or after drying). Activation of the device would result in samples of air being drawn into the device and analyzed for the presence of the taggant. When the hands are slowly placed in front of the device, a sample of air (gas) containing the taggant would be detected and a conspicuous light would turn from red or yellow to green. This light would remain green for a period of time (such as 10 minutes) so that the patient would be assured that the healthcare worker had washing his/her hands recently. A yellow or red indicator would signal to the patient that the healthcare worker needed to wash the hands before touching the patient.

In view of the above, the present invention provides the capability of continuously, monitoring subject compliance in hand hygiene practices, using the detection of taggants in hand washing agents as a surrogate for a hand washing event.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A system for monitoring hand hygiene comprising: a hand washing agent comprising a detectable, volatile compound for application to the hands of a subject; and a detector comprising a sensor and an indicator operably connected to the sensor, wherein the sensor detects the detectable, volatile compound, wherein detection of said detectable, volatile compound by said sensor occurs without physical contact of the hands of said subject with said detector, wherein the detector is in the form of a wearable or portable housing, wherein the detector is a badge.

2. A system for monitoring hand hygiene comprising: a hand washing agent comprising a detectable, volatile compound for application to the hands of a subject; and a detector comprising a sensor and an indicator operably connected to the sensor, wherein the sensor detects the detectable, volatile compound, wherein detection of said detectable, volatile compound by said sensor occurs without physical contact of the hands of said subject with said detector, wherein the detector is located at a particular location, said system further comprising a means for ascertaining subject identity wherein said means for ascertaining subject identity notifies a central computer system when a subject enters a particular location and wherein said means for ascertaining subject identity waits for the subject to wash his/her hands before leaving wherein said means for ascertaining subject identity is operably connected to an entry means which does not permit the subject to enter, to exit or to enter or exit a location unless the detector has ascertained that the subject as performed appropriate hand hygiene measures.

3. A system for monitoring hand hygiene comprising: a hand washing agent comprising a detectable, volatile compound for application to the hands of a subject; and a detector comprising a sensor and an indicator operably connected to the sensor, wherein the sensor detects the detectable, volatile compound, wherein detection of said detectable, volatile compound by said sensor occurs without physical contact of the hands of said subject with said detector, said system further comprising a means for active detection of the detectable, volatile compound, wherein the means for active detection of the detectable, volatile compound is a suction pump that directs air flow to the sensor, wherein said suction pump is activated by an individual before handwashing or which is automatically activated by a means for establishing subject identity wherein, when said subject approaches a subject identification means mounted in close proximity to a hand washing station, it immediately begins a countdown process activating said detector.

4. The system according to claim 3 wherein said detector must detect the presence of a detectable, volatile compound within a finite period after said identification means is activated or an indicator provides feedback, locally, remotely or both, that the subject has not washed his/her hands.

* * * * *